United States Patent
Miklavcic et al.

(10) Patent No.: US 7,306,940 B2
(45) Date of Patent: Dec. 11, 2007

(54) ELECTROPORATION DEVICE AND METHOD, DELIVERING A MODULATED SIGNAL UNDER CONTINUOUS CONTROL OF CELL ELECTROPERMEABILIZATION

(75) Inventors: Damijan Miklavcic, Ljubljana (SI); Lluis Mir, Villejuif (FR); Eberhard Neumann, Bielefeld (DE); Bertil Persson, Lund (SE)

(73) Assignee: IGEA S.r.l., Carpi (IT)

( * ) Notice: Subject to any disclaimer, the term of this patent is extended or adjusted under 35 U.S.C. 154(b) by 689 days.

(21) Appl. No.: 10/274,738

(22) Filed: Oct. 21, 2002
(Under 37 CFR 1.47)

(65) Prior Publication Data

US 2004/0039327 A1    Feb. 26, 2004

Related U.S. Application Data

(63) Continuation of application No. PCT/IT01/00195, filed on Apr. 20, 2001.

(30) Foreign Application Priority Data

Apr. 21, 2000   (IT)   ................ TO2000A0390

(51) Int. Cl.
    *C12M 3/00*   (2006.01)
(52) U.S. Cl. ................ 435/285.2; 435/173.5; 435/173.6

(58) Field of Classification Search ........... None
See application file for complete search history.

(56) References Cited

U.S. PATENT DOCUMENTS 5,019,034 A * 5/1991 Weaver et al. ............ 604/20
5,134,070 A    7/1992 Casnig ..................... 435/173

FOREIGN PATENT DOCUMENTS

| WO | WO 96/39531   | 12/1996 |
| WO | WO 00/20554   | 4/2000  |
| WO | WO 01/07583 A1| 2/2001  |
| WO | WO 01/07584 A1| 2/2001  |

* cited by examiner

*Primary Examiner*—David Redding
(74) *Attorney, Agent, or Firm*—David A. Farah; Sheldon Mak Rose & Anderson PC

(57) ABSTRACT

An electroporation device having a signal generating circuit (3) connectable at the output to electrodes (5) fittable to a substrate (35) having cells. The electrodes (5) produce an electric field which induces permeabilization of the cell membranes to facilitate introduction of substances into the cells. The amplitude of the signal (12) applied to the electrodes is closed-loop controlled on the basis of the impedance ($Z(\omega)$) of the substrate, so as to regulate the amplitude of the signal following a reduction in impedance caused by permeabilization of the cell membranes.

16 Claims, 3 Drawing Sheets

ELECTROPORATION DEVICE AND METHOD, DELIVERING A MODULATED SIGNAL UNDER CONTINUOUS CONTROL OF CELL ELECTROPERMEABILIZATION

CROSS-REFERENCE TO RELATED APPLICATION

This application claims priority from PCT application PCT/IT01/00195 filed Apr. 20, 2001 and titled "Electroporation Device And Method, Delivering a Modulated Signal Under Continuous Control of Cell Electropermeabilization," and claims benefit of Italian patent application TO2000A000390, filed Apr. 21, 2000; the contents of which are incorporated by reference herein in their entirety.

TECHNICAL FIELD

The present invention relates to an electroporation device and method, delivering a modulated signal under continuous control of cell electropermeabilization.

BACKGROUND ART

As is known, recent biological, microbiological and pharmacological applications involve introducing molecules into cells, which is done by inserting the molecules through cell membranes.

The molecules may be inorganic substances (e.g., drugs) or organic molecules (cells are known to be inserted, for example, with DNA molecules).

Molecules are introduced using various methods, including:

viral vectoring: associating the molecule with a virus, which is then introduced into the cell;

chemical vectoring: associating the molecule with a chemical substance for reducing the resistance of the cell membrane and so permitting introduction of the molecule into the cell; and ballistic methods: accelerating the molecule so that it strikes and penetrates the cell membrane.

Known methods involve several drawbacks, including: risk of immunity reaction to the vector; production difficulties and poor stability of the vector itself (viral vectoring); ineffectiveness, toxicity and poor selectivity (chemical vectoring). As for ballistic methods, these only apply to surface cells.

New so-called electroporation methods have recently been devised, which provide for briefly applying a strong electric field to the cells to permeabilize, and so enable substances to penetrate, the cell membrane.

One problem posed by known electroporation methods is establishing the value of the electric field applied, which must be high enough to permeabilize the cell membrane, but not so high as to cause irreversible damage to the cell.

More specifically, known electroporation devices and methods employ a fixed output voltage value (determined, for example, experimentally), so that, in certain operating conditions, the electric field may be too low, thus preventing introduction of the substances, and/or too high, thus resulting in irreversible damage to the cell.

DISCLOSURE OF INVENTION

It is an object of the present invention to provide an electroporation device and method designed to eliminate the drawbacks of known electroporation devices and methods.

According to the present invention, there is provided an electroporation device as described in Claim 1.

The present invention also relates to an electroporation method as described in claim 13.

BRIEF DESCRIPTION OF THE DRAWINGS

A preferred, non-limiting embodiment of the invention will be described by way of example with reference to the accompanying drawings, in which.

BEST MODE FOR CARRYING OUT THE INVENTION

Figure 1:
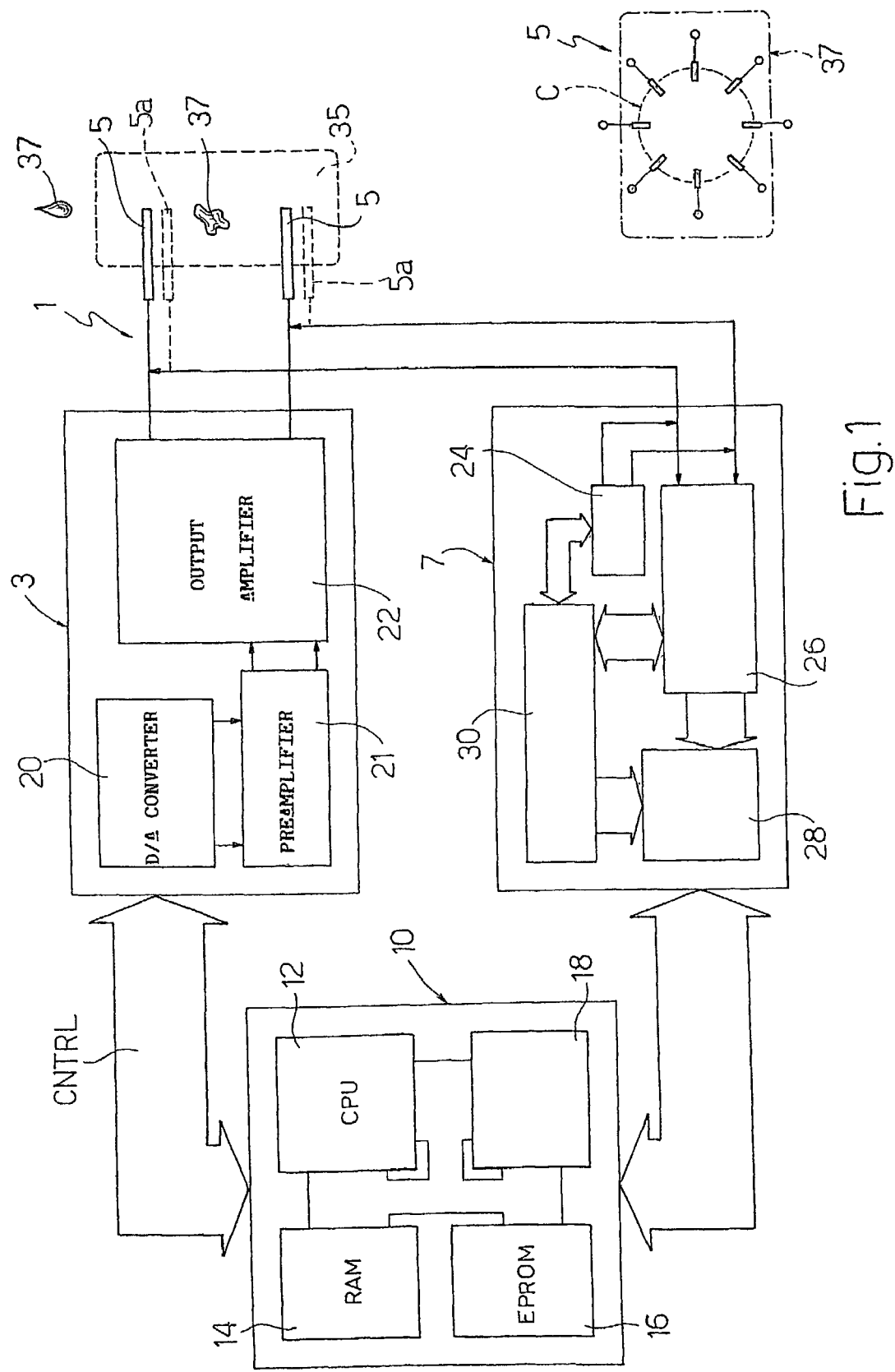
FIG. 1 shows, schematically, an electroporation device in accordance with the teachings of the present invention.

Number 1 in FIG. 1 indicates as a whole an electroporation device.

Device 1 comprises a signal generator, in particular a pulse generator 3 having at least two output electrodes 5; a measuring system 7 connected to output electrodes 5; and an electronic control unit 10 for controlling pulse generator 3 and measuring system 7.

Electronic control unit 10 comprises at least one microprocessor 12 co-operating with memory devices, e.g. a RAM memory 14 and EPROM memory 16; and interface devices 18.

Pulse generator 3 comprises a digital/analog D/A converter 20, which receives a control signal CNTRL from unit 10 and co-operates at the output with a preamplifying circuit 21; preamplifying circuit 21 has an output connected to the input of a power amplifier 22 in turn having an output communicating with electrodes 5; and electrodes 5, in the example embodiment shown, are each defined by a flat, rectangular metal blade to which the output signal from power amplifier 22 is applied.

The electrodes may, of course, differ in shape, structure and size from those shown, e.g. may be designed for use in a laparoscopy process.

Electrodes 5 may also comprise a number of electric terminals (FIG. 1) arranged, for example, along a circular (triangular or hexagonal) closed-loop path C and supplied sequentially in pairs with the output signal from power amplifier 22. In which case, a multiplexer circuit (not shown) is provided to select and supply pairs of electrodes, e.g. pairs of electrodes on opposite sides of circular path C. The multiplexer circuit may also be associated with a circuit (not shown) for determining the impedance between pairs of electrodes in the number; and a circuit (not shown) for directing the signal to an automatically selected pair of electrodes. The pair may be selected automatically by comparing the measured impedance and selecting the pair (or the pairs) of electrodes whose impedance has a predetermined relationship with, e.g. is greater than, the impedance of the other pairs.

Measuring system 7 comprises an oscillating circuit 24 for supplying electrodes 5 with an excitation signal; and a converting circuit 26 supplied by electrodes 5 with a signal in response to the excitation signal. Converting circuit 26 co-operates with a memory 28 (e.g. a RAM memory) which is also connected to a known measuring circuit 30, which also co-operates with converting circuit 26 and with oscillating circuit 24. It is noted that the measurement of the impedance may be done both in the frequency domain or in the time domain.

Figure 2:
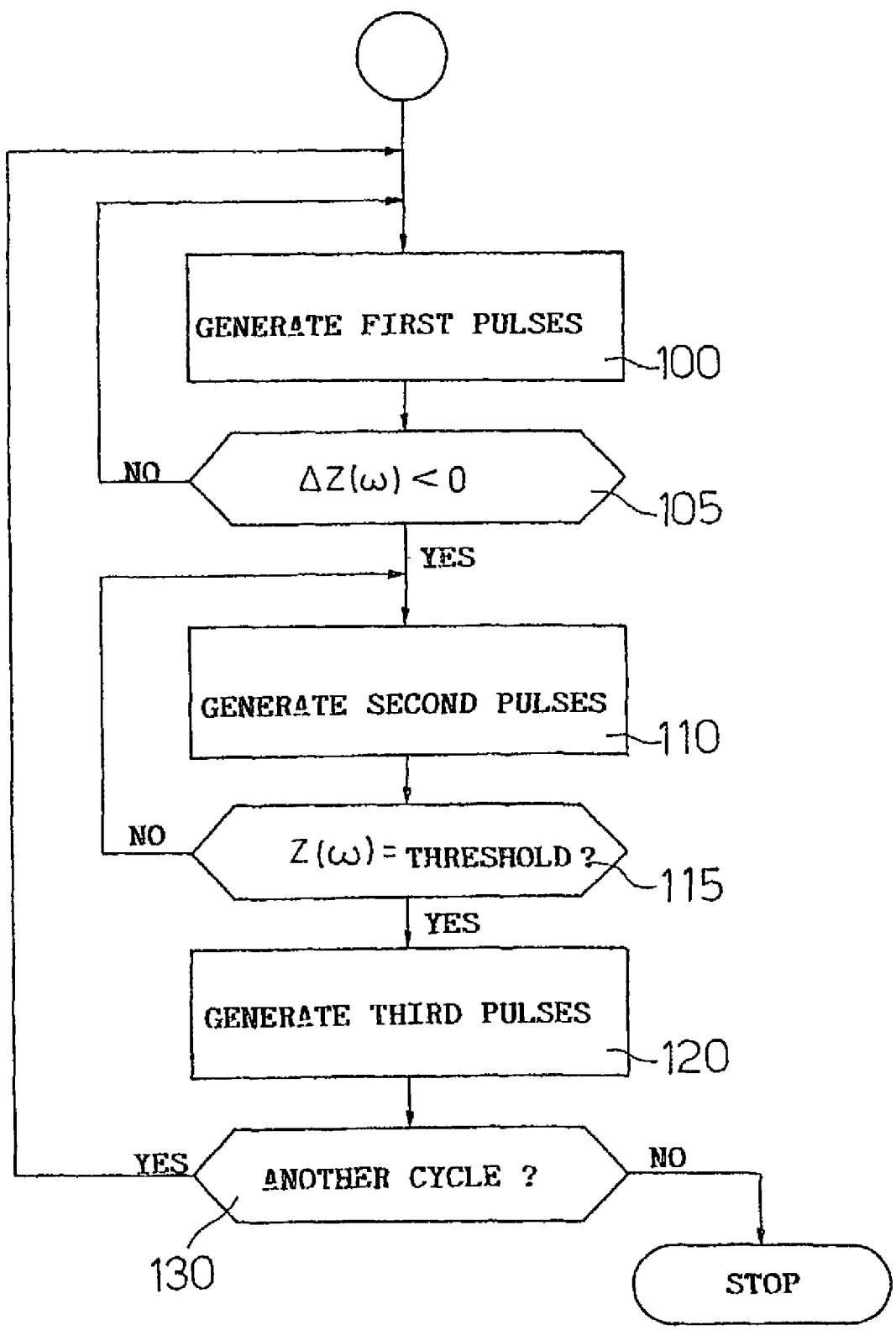
FIG. 2 shows a logic operating diagram of the FIG. 1 device.

FIG. 2 shows a block diagram of the operations performed by electroporation device 1 under the control of electronic unit 10.

Figure 3:
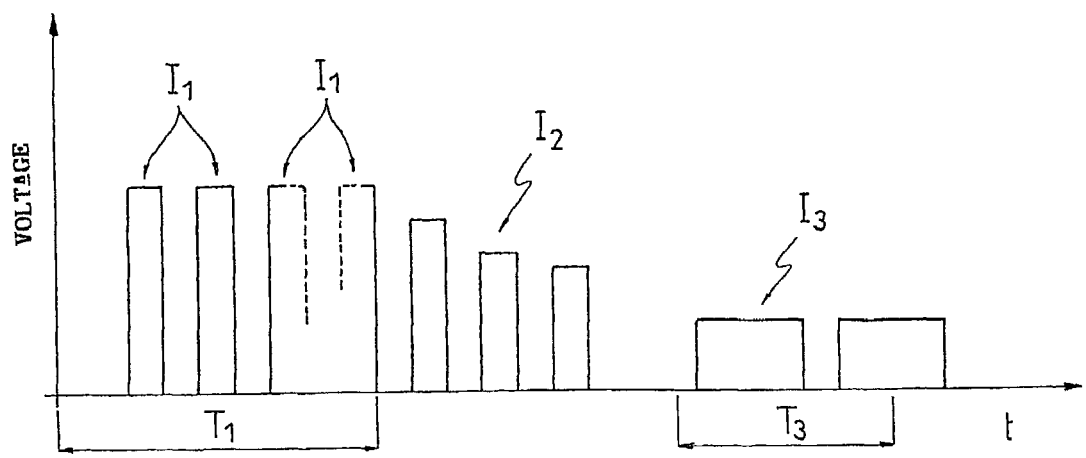
FIGS. 3 and 3a show signals produced by the FIG. 1 device.

When device 1 is activated, a first block 100 generates a first control signal CNTRL1 for pulse generator 3, which, in response, produces a first number of first voltage pulses I1 which are applied to electrodes 5 (FIG. 3). First pulses I1, which are preferably rectangular, are of constant amplitude and width and equally spaced in the time.

The voltage value of each first pulse depends on the geometry of electrodes 5, while the total application time T1 of the first pulses depends on the instant at which a change in impedance is detected.

More specifically, block 100 is followed by a block 105, which measures the impedance $Z(\omega)$ between electrodes 5. More specifically, block 105 calculates the impedance variation $\Delta Z(\omega)$ between two successive instants t−1 and t, i.e. $\Delta Z(\omega) = \Delta Z(\omega)_t - \Delta Z(\omega)_{t-1}$.

When the impedance variation $\Delta Z(\omega)$ remains substantially equal to zero (i.e. no noticeable change in impedance), block 105 goes back to block 100. When the impedance variation is less than zero (i.e. impedance decreasing and therefore changing with time), block 105 is followed by a block 110.

Block 110 generates a second control signal CNTRL2 for pulse generator 3, which, in response, produces a second number of second pulses I2 which are applied to electrodes 5 (FIG. 3). The amplitude of second pulses I2 depends on the impedance $z(\omega)$ measured between electrodes 5. Impedance $Z(\omega)$ is measured in known manner by measuring system 7, and the measured impedance value is supplied to electronic control unit 10, which, in response, controls the amplitude of second pulses I2.

More specifically, the amplitude of second pulses I2 decreases alongside a reduction in impedance, increases alongside an increase in impedance, and may also increase when impedance remains constant for a given length of time.

The impedance measurement may comprise measuring the absolute impedance value $|Z(\omega)|$ or calculating the real impedance part Zr, the imaginary part jZo and angle $\alpha = \text{arctg}(Zo/Zr)$.

Instead or in addition of impedance calculating the device could also measure other electric characteristics for instance, admittance, resistivity or conductivity including dynamic resistance or dynamic conductivity. The device could also measure current at constant voltage and vice versa.

On average, second pulses I2 have a lower amplitude than the first pulses.

Second pulses I2 are generated until the measured impedance reaches a predetermined lower threshold value zp indicating permeability of the cell membranes has been attained and no further changes in impedance between successive pulses are detected (block 115 following block 110). Once the lower threshold value is reached, block 115 goes on to a block 120, thus providing for closed-loop control of the amplitude of pulses I2.

Figure 3A:
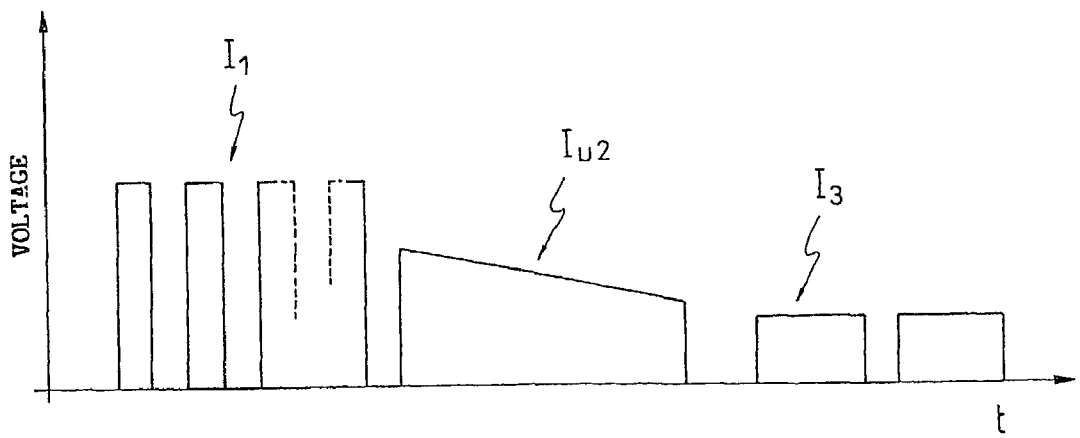

Alternatively, block 110 may produce a single pulse Iu2 (FIG. 3a) of an amplitude depending on the impedance $Z(\omega)$ measured between electrodes 5, thus providing for closed-loop control of the amplitude of pulse Iu2.

More specifically, like pulses I2, the amplitude of single pulse Iu2 decreases alongside a reduction in impedance, increases alongside an increase in impedance, and may also increase when impedance remains constant for a given length of time.

More specifically, pulse Iu2 normally decreases in amplitude as impedance decreases with time, and the closed-loop control regulates, by decreasing, the amplitude of pulse Iu2. The amplitude of pulse Iu2 may also increase when impedance remains constant for a given length of time.

Block 120 generates a third control signal CNTRL3 for pulse generator 3, which, in response, produces a third number of third pulses I3 which are applied to electrodes 5 (FIG. 3). Third pulses I3 have a much lower amplitude than first and second pulses I1 and I2; are, for example, rectangular in shape; are applied for a predetermined time T3; are each of a time width greater than that of pulses I1 and I2; and may also comprise a single pulse I3.

Block 120 is followed by a block 130, which enquires whether another electroporation cycle is to be performed. If it is, block 130 goes back to block 100; if it is not, electroporation is interrupted.

In actual use, electrodes 5 are applied to a tissue portion 35 (shown schematically in FIG. 1) containing live cells. The tissue portion may be one forming part of a live being (human, animal or vegetable) or one containing cells removed from a live being (human, animal or vegetable). Tissue portions are also understood to include cultures of uni- or multicellular organisms (prokaryotes or eukaryotes). In other words, a tissue portion is intended to mean, in general, a substrate of any nature on which live cells or cellular organisms are present.

Tissue portion 35 is also applied with a substance (organic or inorganic or biopolymeric) 37 to be introduced into the cells. The substance may be applied in a number of different ways, some of which are listed below by way of non-limiting examples:

direct application of the substance to the tissue portion, e.g. by applying the tissue portion with a fluid containing the substance;

indirect application of the substance, e.g. by introducing the substance into the circulatory system of the tissue portion;

injecting the substance, e.g. using needlelike electrodes 5, each having an inner conduit containing the substance to be injected into the tissue portion. The substance may also be injected using needles separate from the electrodes.

The substance introduced may be inorganic or organic or biopolymeric, e.g.

a nucleic acid;

a DNA molecule containing regulatory sequences and sequence coding for therapeutic genes or genes of interest for biomedical or biotechnological purposes;

an oligonucleotide, whether natural (phosphodiesters) or modified (inside the backbone of the oligonucleotide, such as phosphosulfates, or at the extremities, by addition of groups to protect the oligonucleotides from digestion of nucleoasis; the description of oligonucleotide modifications being non-limiting);

a protein or peptide, whether natural or genetically or chemically modified, extracted from natural sources or obtained by synthesis, or a molecule simulating the structure of a protein or peptide, whatever its structure;

a cytotoxic agent, in particular, the antibiotic bleomycin or cisplatinum;

a penicillin;

a pharmacological agent other than a nucleic acid.

Device 1 is activated to generate first pulses I1, which are applied to electrodes 5 to produce an electric field, which is directed into the tissue portion to commence permeabilization of the tissue cell membranes. Permeabilization is more intense close to electrodes 5 (where the electric field is stronger) and becomes gradually less as the distance from the electrodes increases. Following permeabilization of the cell membranes, the electric characteristics of the tissue change. More specifically, conductivity of the tissue increases, so that tissue impedance decreases.

Second pulses I2 (or pulse Iu2) are then applied, the value of which depends on the tissue impedance measured. Permeabilization of the cell membranes is therefore followed by a fall in impedance, which is detected by measuring system 7 to enable an automatic closed-loop reaction of device 1 to reduce the amplitude of pulses I2 (or pulse Iu2) and hence the intensity of the electric field applied. Similarly, poor permeabilization of the cell membranes is marked by little variation in impedance, which is detected by measuring system 7 to enable an automatic closed-loop reaction of device 1 to increase the amplitude of pulses I2 (or pulse Iu2) and hence the intensity of the electric field applied.

The amplitude of the pulses (or single pulse) is therefore regulated according to the instantaneous electric characteristics of the tissue, which in turn depend on the extent to which the cell membranes are permeabilized. This therefore prevents damage to the cells caused by too high an electric field being applied to an already permeabilized tissue. At the same time, in the event the tissue fails to "respond" to the pulses applied, i.e. permeabilization of the cell membranes is not initiated, the amplitude of the pulses (or single pulse) and of the electric field is increased. Generating the second pulses (or pulse) ensures the whole of the tissue portion area between the electrodes is permeabilized.

Pulses I3 are then applied to facilitate introduction of charged high-molecular-mass substances, e.g. DNA.

Substance 37 is then introduced into the cells.

The knowledge gathered by the Applicant indicates that applying at least one pulse of an amplitude adjustable according to the measured impedance provides for achieving a high degree of permeabilization of the cell membranes, while at the same time preventing damage to the cell tissue.

Clearly, changes may be made to the device as described herein without, however, departing from the scope of the present invention.

Figure 4:
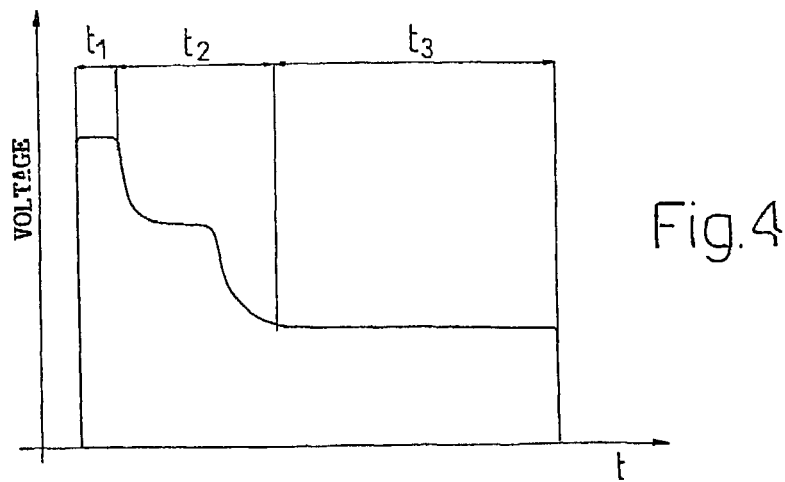
FIG. 4 shows a variation of the FIGS. 3, 3a signals.

As opposed to being measured using the same pair of electrodes used to apply the electric field to substrate 35, as in the embodiment described above, the impedance of substrate 35 may also, obviously, be measured by a separate pair of auxiliary electrodes 5a (shown schematically with dotted lines in FIG. 1) close to electrodes 5, electrically separated from electrodes 5 and placed in contact with tissue portion 35 to be permeabilized. Continuous signals, as opposed to pulses, may be generated. In which case, as opposed to producing a number of separate pulses (I1, I2, I3), signal generator 3 may generate a single continuous analog signal (FIG. 4) comprising three adjacent portions respectively corresponding to pulses I1, I2, I3. The continuous analog signal may comprise a first high-amplitude portion corresponding to first pulses I1; a second portion (corresponding to pulses I2) having an amplitude varying as a function of measured impedance $Z(\omega)$; and a third lower-amplitude portion corresponding to pulses I3. pulse sequence. The sequences may also be of the exponential type and may also comprise bipolar pulses to avoid the polarixation of the electrodes.

What is claimed:

1. An electroporation device comprising a signal generator comprising a pulse generator having at least two output electrodes fittable to a substrate comprising cells; said electrodes producing, in said substrate, an electric field which induces permeabilization of the membranes of said cells to facilitate introduction of substances into the cells; the device further comprising a measuring system and an electronic control unit, which constitute a regulator for controlling characteristic quantities of the signal (I2) generated by the signal generator and applied to the substrate on the basis of the impedance ($Z(\omega)$) measured in the substrate; said impedance ($Z(\omega)$) being a function of the degree of permeabilization attained by the membranes of said cells,
   characterized in that said signal generator generates:
   a number of first pulses (I1) applied to the electrodes; each first pulse having a constant amplitude;
   at least one second pulse (I2; Iu2) applied to the electrodes; said second pulse (I2; Iu2) having an amplitude which is a function of the impedance $Z(\omega)$ measured in the substrate;
   at least one third pulse (I3) applied to the electrodes; said third pulse (I3) having a lower amplitude than the first pulses (I1) and the second pulse (I2; Iu2).

2. The device as claimed in claim 1, wherein said regulator reduces the amplitude of said at least second pulse (I2) as the impedance (Z(107 ) decreases.

3. The device as claimed in claim 1, wherein said regulator increases the amplitude of said at least one second pulse (I2) when said impedance ($Z(\omega)$) increases or remains noticeably constant.

4. The device as claimed in claim 1, wherein an impedance change detector is provided permitting generation of said second pulse until the measured impedance reaches a predetermined lower threshold value indicating permeability of the cell membranes has been achieved; said impedance change detector initiating generation of said third pulse upon the lower threshold value being reached.

5. The device as claimed in claim 1, wherein said electrodes comprise a number of electrodes arranged along a closed path, and supplied sequentially in pairs with the output signal of said signal generator.

6. The device as claimed in claim 5, wherein the one or more than one impedance measuring device measuring system determines the impedance between pairs of electrodes in said number; and a signal director for directing said signal to an automatically selected pair of electrodes; said pair being selected automatically by comparing the impedances measured, and by selecting the pair of electrodes whose impedance has a predetermined relationship with respect to the impedances of the other pairs.

7. The device as claimed in claim 6, wherein said pulse generator produces a single pulse (Iu2) having an amplitude adjustable on the basis of said electric characteristics ($Z(\omega)$) measured in the substrate.

8. An electroporation method comprising the steps of:
   providing an electroporation device according to claim 1;
   generating an electric signal using the electroporation device; and
   applying said electric signal to a substrate comprising cells, to produce, in said substrate, an electric field which induces permeabilization of the membranes of said cells to facilitate introduction of a substance into the cells;
   characterized by comprising the step of regulating characteristic quantities of the signal (I2) on the basis of electric characteristics ($Z(\omega)$) measured in the substrate; said electric characteristics ($Z(\omega)$) being functions of the degree of permeabilization attained by the membranes of said cells.

9. The method as claimed in claim 8, wherein said regulating step comprises the step of controlling the amplitude of the signal on the basis of said electric characteristics ($Z(\omega)$).

10. The method as claimed in claim 8, wherein said regulating step comprises the step of:
measuring the impedance of said substrate; and
controlling the characteristic quantities of the signal on the basis of said impedance ($Z(\omega)$).

11. The method as claimed in claim 10, wherein said regulating step comprises the step of reducing the amplitude of said signal as said impedance decreases.

12. The method as claimed in claim 10, wherein said regulating step comprises the step of increasing the amplitude of said signal when said impedance increases or remains noticeably constant.

13. The method as claimed in claim 8, wherein said step of generating a signal comprises the step of generating a number of pulses (I2); each pulse having an amplitude adjustable on the basis of said electric characteristics ($Z(\omega)$) measured in the substrate.

14. The method as claimed in claim 8, wherein said step of generating a signal comprises the step of generating a single pulse (Iu2); said single pulse having an amplitude adjustable on the basis of said electric characteristics ($Z(\omega)$) measured in the substrate.

15. The method as claimed in claim 1, characterized in that said step of generating at least one second pulse (Iu2) is performed until the measured impedance reaches a predetermined lower threshold value indicating permeability of the cell membranes has been achieved; said third pulse being generated upon the lower threshold value (Zp) being reached.

16. The method as claimed in claim 8, characterized in that said substance comprises an organic compound selected from the group consisting of a nucleic acid, a DNA molecule, an oligonucleotide, a cytotoxic agent and a penicillin.

* * * * *

UNITED STATES PATENT AND TRADEMARK OFFICE
CERTIFICATE OF CORRECTION

PATENT NO. : 7,306,940 B2
APPLICATION NO. : 10/274738
DATED : December 11, 2007
INVENTOR(S) : Damijan Miklavcic et al.

It is certified that error appears in the above-identified patent and that said Letters Patent is hereby corrected as shown below:

Claim 1:

Col. 6, Line 18, replace "(12; Iu2)" with --(I2; Iu2)--

Col. 6, Line 19, replace "(12; Iu2)" with --(I2; Iu2)--

Claim 2:

Col. 6, Line 27, replace "(Z(107)" with --(Z(ω))--

Signed and Sealed this

Third Day of June, 2008

JON W. DUDAS
*Director of the United States Patent and Trademark Office*